United States Patent [19]

Green et al.

[11] 4,089,977

[45] May 16, 1978

[54] POLYMERIC ANTI-MICROBIAL AGENT

[75] Inventors: Harold A. Green, Havertown, Pa.; John J. Merianos, Jersey City; Alfonso N. Petrocci, Glen Rock, both of N.J.

[73] Assignee: Kewanee Industries, Bryn Mawr, Pa.

[21] Appl. No.: 744,617

[22] Filed: Nov. 24, 1976

[51] Int. Cl.$^2$ .................. A01N 9/20; C07C 87/22
[52] U.S. Cl. .................. 424/329; 260/567.6 H; 260/567.6 P
[58] Field of Search ............. 424/329; 260/567.6 P, 260/567.6 H

[56] References Cited

U.S. PATENT DOCUMENTS

| | | | |
|---|---|---|---|
| 3,334,138 | 8/1967 | Feeman | 260/567.6 P |
| 3,769,346 | 10/1973 | Boissier et al. | 260/567.6 P |

*Primary Examiner*—Leonard Schenkman
*Attorney, Agent, or Firm*—Arthur A. Jacobs

[57] ABSTRACT

A polymeric quaternary ammonium compound, or a mixture of polymeric quaternary ammonium compounds, having the formula $Z[CH_2CHOHCH_2-N^{\oplus}(CH_3)_2]_nCH_2CHOHCH_2—Z + nX^-$, wherein Z is either X or the radical $—N(CH_3)_2$; where X is halogen of atomic weight greater than 34; and $n$ is an integer of from 2 to 20.

6 Claims, No Drawings

POLYMERIC ANTI-MICROBIAL AGENT

This invention relates to polymeric non-foaming anti-microbial and preservative agents. More specifically, it relates to polymeric quaternary ammonium compounds or mixtures of such compounds, having the formula $Z[CH_2CHOHCH_2N^{\oplus}(CH_3)_2]_nCH_2CHOHCH_2—Z + nX$, in which Z is either X, or the radical $—N(CH_3)_2$; where X is a halogen of atomic weight greater than 34; and $n$ is integer of from 2 to 20.

The polymeric quaternary ammonium compounds of the present invention are not only very potent anti-microbials, but are non-foaming. This makes them especially suited for use in the control of microoganisms in re-circulating water systems such as in paper manufacturing, air conditioning, humidifiers, grinding lubricants, and in other systems where foaming is a burdensome problem or interferes with the normal anti-microbial behavior of desirable additives. The compounds of the present invention are also effective in keeping relatively still or standing waters, such as in swimming pools or the like, free from microbes.

Another very imporatant feature of the compounds of the present invention is their sustained anti-microbial effectiveness even in the presence of non-ionic emulsifiers. Ordinarily, quaternary ammonium biocides lose their effectiveness in the presence of non-ionic emulsifiers, often to the point where they can no longer function as anti-microbials. This often precludes their use in cosmetics, which usually require the presence of non-ionic surfactants. The products of the present invention, however, maintain their effectiveness even when relatively large quantities of non-ionic surfactants are present in the system.

The following examples illustrate the preparation of products embodying the present invention.

EXAMPLE 1

300 grams of a 13% aqueous solution of NaCl in water was cooled to 10° C, and 100 ml. of conc. HCl (1 mole of HCl) was added.

92.5 grams of epichlorohydrin (1 mole) was added slowly to the reaction mixture over a period of 2 hours with continued stirring and cooling, whereby the mixture remained below 30° C. The reaction mixture separated into two layers. The lower layer weighed 145 grams, and, upon distillation at atmospheric pressure and at a temperature of about 172°–175° C, yielded 119 grams of 1,3-dichloro-2-propanol (92% yield). The reaction may be expressed as follows:

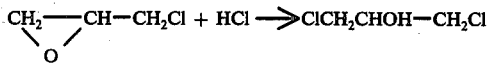

EXAMPLE 2

1072 grams of a 42% aqueous solution of dimethylamine (10 moles) and 129 grams of 1,3-dichloro-2-propanol (1 mole) were mixed and heated in an autoclave at about 80°–90° C for about 2 hours, after which time an analysis for ionic chloride showed that the reaction was almost complete (5.85% found; 5.92% calc'd).

The reaction misture was treated with 300 grams of 50% aqueous NaOH, and the unreacted dimethylamine recovered. The top layer of the separated solution weighed 169 grams and yielded 139 grams of 1,3-bis-dimethylamino-2-propanol (95% of theory) when distilled at atmospheric pressure and at a temperature of about 180°–187° C.

The reaction may be expressed as follows:

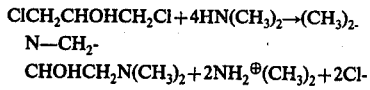

EXAMPLE 3

146 grams of 1,3-bis-dimethylamino-2-propanol (1 mole), 129 grams of 1,3-dichloro-2-propanol (1 mole) and 300 grams of water were heated, with stirring, at about 40° to about 90° C for about 2–12 hours (the lower the temperature the longer the heating time), after which analysis for ionic chloride showed that the reaction was about 98% complete. The product was stripped of volatile materials in vacuo until the residue contained about 50% active material.

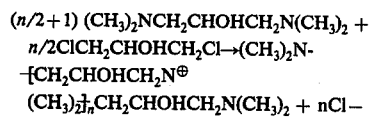

Analysis of the product from Example 3, for both total chlorine and ionic chlorine, indicated that a small fraction of the polymeric chains had either one or two chlorine termini. Repeated syntheses and analysis indicated that about 0.01 to about 0.04 moles of non-ionic chlorine were present in the final product, either at one terminus of a chain, or at both termini. Therefore, some of the polymeric material has the structure:

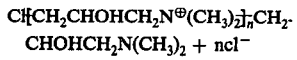

or

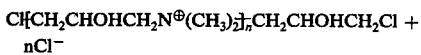

but most of the polymeric material has the structure:

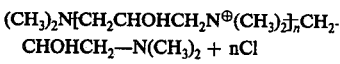

It was found that the number of chlorine termini (non-ionic chlorine) could be reduced to practically nothing if a slight molar excess (of from about 5%–10%) of dimethylamine above the calculated amount was used in the procedure of Example 3. The same effect could be achieved by adding 5%–10% dimethylamine to the product of the equimolar mixture and heating. However, the product resulting from the use of about 1:1 molar ratio of reactants, the product resulting from the use of about a 5% to 10% excess of dimethylamine and the product made by subsequent heating with dimethylamine showed no noticable difference in either anti-microbial or non-foaming properties.

The following examples illustrate the anti-microbial properties of the products of the present invention.

EXAMPLE 4

The product made in Example 3 was diluted in distilled water to various test concentrations, and 50 ml aliquots of these solutions were transferred aseptically to corresponding previously sterilized cotton-stoppered 125 ml. Erlenmeyer flasks, whereby there were provided a set of flasks, each at a different concentration of material to be tested. Each flask was inoculated with 0.5 ml. of a 1/10 nutrient broth dilution of a 24-hour nutrient broth culture of Aerobacter aerogenes.

Another set of flasks, containing the same variation of concentrations of the product of Example 3, were similarly prepared and inoculated with 0.5 ml. of a 1/10 nutrient broth dilution of the 24-hour nutrient broth culture of Pseudomonas aeruginosa.

At 30 and 60 minutes intervals following inoculation, a 1 ml. aliquot was removed from each flask and to it was added 9ml. of a sterile azololectin/"Tween 80" neutralizer. From this, additional 10-fold serial dilutions were prepared in sterile neutralizer solutions.

Agar plates were prepared from $1 \times 10^{-2}$ and $1 \times 10^{-3}$ dilutions.

A control of sterile distilled water was similarly inoculated and aliquots were made at the same time intervals and using the same type agar plates, at $1 \times 10^{-4}$, $1 \times 10^{-5}$, and $1 \times 10^{-6}$ dilutions.

The number of surviving organisms for various concentrations at different times of exposure indicated in the tables by different test numbers, were noted, and a comparison between them was made.

The results are shown as follows:

TABLE 1

Products of Example 3, acting for 30 minutes on *Aerobacter aerogenes*, at a concentration of $10.05 \times 10^6$ organisms per ml.

| Concentration of Product in ppm | Number of Surviving Organisms $\times 10^{-2}$ | |
|---|---|---|
| | Test No. 1 | Test No. 2 |
| 10 | 78 | 91.5 |
| 15 | 50.5 | 45 |
| 20 | — | 33.5 |
| 25 | 20 | 25 |
| 40 | 45 | — |
| 50 | 0 | 0 |
| 75 | 0 | 0 |
| 100 | 0 | 0 |
| 200 | 0 | 0 |

TABLE 2

Product of Example 3, acting for 60 minutes on *Aerobacter aerogenes*, at a concentration of $10.05 \times 10^6$ organisms per ml.

| Concentration of Product in ppm | Number of Surviving Organisms $\times 10^{-2}$ | | |
|---|---|---|---|
| | Test No. 1 | Test No. 2 | Test No. 3 |
| 10 | 27 | 30 | — |
| 15 | 13 | 16 | — |
| 20 | — | 9.5 | — |
| 25 | 4 | 4 | — |
| 40 | 0 | 0 | 0 |
| 50 | 0 | 0 | 0 |
| 75 | 0 | 0 | 0 |
| 100 | 0 | 0 | 0 |
| 200 | 0 | 0 | 0 |

TABLE 3

Product of Example 3, acting for 30 minutes on *Pseudomanas aeruginosa*, at a concentraton of $14.05 \times 10^6$ organisms per ml.

| Concentration of Product in ppm | Number of Surviving Organisms $\times 10^{-2}$ | | |
|---|---|---|---|
| | Test No. 1 | Test No. 2 | Test No. 3 |
| 10 | — | — | — |
| 15 | 263 | — | — |
| 20 | — | 138 | — |
| 25 | 92 | 68 | — |
| 30 | | 49.5 | — |
| 40 | 36.5 | 30 | — |
| 50 | 8 | 8 | 8.5 |
| 75 | 0 | 0 | 0 |
| 100 | 0 | 0 | 0 |
| 200 | 0 | 0 | 0 |

TABLE 4

Product of Example 3, acting for 60 minutes on *Pseudomonas aeruginosa*, at a concentration of $14.05 \times 10^6$ organisms per ml.

| Concentration of Product in ppm | Number of Surviving Organisms $\times 10^{-2}$ | | |
|---|---|---|---|
| | Test No. 1 | Test No. 2 | Test No.3 |
| 10 | 201.5 | — | — |
| 15 | 165 | — | — |
| 20 | — | 41.5 | — |
| 25 | 57 | 25.5 | — |
| 30 | — | 17 | — |
| 40 | 10 | 8 | — |
| 50 | 0 | 0 | 0 |
| 75 | 0 | 0 | 0 |
| 100 | 0 | 0 | 0 |
| 200 | 0 | 0 | 0 |

Tables 1, 2, 3, and 4 show that the product made in Example 3, in testing, caused a complete absence of surviving Aerobacter aerogenes organisms after 30 minutes exposure when applied at a concentration of 50 ppm, and after 60 minutes exposure when applied at a concentration of 40 ppm. Test against Pseudomonas aeruginosa showed a complete absence of surviving organisms after 30 minutes exposure when applied at a concentration of 75 ppm, and after 60 minutes exposure when applied at a concentration of 50 ppm.

The following examples illustrate the non-foaming properties of the products of the present invention:

EXAMPLE 5

A graduated blender cylinder is rinsed with distilled water. 100 ml. of aqueous test solution is added down the walls of the blender so as to cause no foam. The blender is turned to high speed for exactly 5 seconds, and, upon turning the blades off, timing is started with a stop watch, while, at the same time the foam height read in mm. from the 100 ml. mark. The foam half-life is defined as the time it takes for liquid to drain out of the foam and reach the 50 ml mark.

The results were as follows:

TABLE 9

| Sample | ppm | Foam Height in mm | Half-Life |
|---|---|---|---|
| Alkyldimethylbenzyl Ammonium Chloride | 50 | 16 | 7.2 sec |
| Product of Example 3 | 50 | 0 | 0 |

EXAMPLE 6

CYLINDER SHAKE TEST 100 ml. of test solution is gently poured down the walls of a 250 ml. graduated cylinder that has a glass stopper. The cylinder is stoppered and inverted 20 times in 15 seconds, finally resting it in an upright position. The foam height is read in cc. from the base of the foam.

TABLE 10

| Sample | ppm | Foam Height in cc | | |
|---|---|---|---|---|
| | | Initial | 1 min. | 5 min. |
| Alkyldimethylbenzyl Ammonium Chloride | 50 | 48 | 35 | 30 |
| Product of Example 3 | 50 | 0 | 0 | 0 |

EXAMPLE 7

Another test used was the standard "Ross-Miles Test" according to the procedure reported in ASTM standards, Designation 1175-53, Part X, 1958, page 878"

which is ASTM test for foaming properties of surface active materials.

TABLE 11

| Sample | ppm | Foam Height in cc. | | |
|---|---|---|---|---|
| | | Initial | 1 min. | 5 min. |
| Alkyldimethylbenzyl Ammonium Chloride | 50 | 35 | 30 | 20 |
| Product of Example 3 | 50 | 0 | 0 | 0 |

The results from Examples 5, 6, and 7 clearly show that the products of this invention are non-foaming, whereas other quaternary ammonium products cause relatively copious foam in aqueous solution.

The invention claimed is:

1. A compound or a mixture of compounds formed by the reaction of equimolar proportions of 1,3-bis-dimethylamino-2-propanol and 1,3-dichloro-2-propanol, the reaction being effected at a temperature of about 40° to about 90° C for about 2 to 12 hours.

2. An antibacterial composition comprising an aqueous solution containing an effective amount of a compound or mixture of compounds formed by the reaction of equimolar proportions of 1,3-bis-dimethylamino-2-propanol and 1,3-dichloro-2-propanol, the reaction being effected at a temperature of about 40° to about 90° C for about 2 to 12 hours.

3. The composition of claim 2 wherein said compound or mixture of compounds is present in a concentration of at least 40 ppm.

4. A method of inhibiting bacteria which comprises applying to said bacteria an antibacterially effective amount of a compound or mixture of compounds formed by the reaction of equimolar proportions of 1,3-bis-dimethylamino-2-propanol and 1,3-dichloro-2-propanol, the reaction being effected at a temperature of about 40° to about 90° C for about 2 to 12 hours.

5. The method of claim 4 wherein the bacteria is Aerobacter aerogenes and wherein the amount of said compound or mixture of compounds is at least 40 ppm of a total treating composition comprising said compound or mixture of compounds and a carrier.

6. The method of claim 4 wherein the bacteria is a Pseudomonas aeruginosa and wherein the amount of said compound or mixture of compounds is at least 50 ppm of a total treating composition comprising said compound or mixture of compounds and a carrier.

* * * * *